United States Patent
Appling et al.

(10) Patent No.: US 7,033,815 B2
(45) Date of Patent: Apr. 25, 2006

(54) BIOSYNTHESIS OF S-ADENOSYLMETHIONINE IN A RECOMBINANT YEAST STRAIN

(75) Inventors: Dean R. Appling, Austin, TX (US); Andrew D. Hanson, Gainesville, FL (US); Sanja Roje, Gainesville, FL (US); Rhonda K. Raymond, Austin, TX (US)

(73) Assignees: Board of Regents, the University of Texas System, Austin, TX (US); University of Florida, Gainesville, FL (US)

( * ) Notice: Subject to any disclaimer, the term of this patent is extended or adjusted under 35 U.S.C. 154(b) by 0 days.

(21) Appl. No.: 10/113,852

(22) Filed: Mar. 29, 2002

(65) Prior Publication Data

US 2002/0192784 A1    Dec. 19, 2002

Related U.S. Application Data (60) Provisional application No. 60/280,333, filed on Mar. 30, 2001.

(51) Int. Cl.
*C12N 9/02* (2006.01)
*C12N 15/00* (2006.01)
*C12N 1/14* (2006.01)
*C12P 21/08* (2006.01)
*C07H 21/04* (2006.01)

(52) U.S. Cl. .............. 435/252.3; 530/387.3; 435/322.1; 435/254.2; 435/325; 435/419; 435/189; 536/23.6; 536/23.2

(58) Field of Classification Search .......... 435/189, 435/320.1, 254.21, 69.1, 325, 419; 536/23.5, 536/23.2; 530/387.3
See application file for complete search history.

(56) References Cited

U.S. PATENT DOCUMENTS

| 4,562,149 | A | 12/1985 | Shiozaki et al. |
| 5,876,996 | A | 3/1999 | Bandman et al. |
| 2002/0010147 | A1 | 1/2002 | Berna |

FOREIGN PATENT DOCUMENTS

WO    WO02/079381 A2 * 10/2002

OTHER PUBLICATIONS

Roje S, Chan SY, Kaplan F, Raymond RK, Horne DW, Appling DR, Hanson AD. Metabolic Engineering in Yeast Demonstrates that S-Adenoosylmethionine Controls Flux through the Methylenetetrahydrofolate Reductase Reaction in Vivo. 2001 J Biol Chem 277:4056-4061.
Neurochemistry that Brain Levels of SAMe in Alzheimer's Patients are Severely Decreased. Life Extension Magazine, Mar. 1997, 4 pgs., http://www.lef.org/magazine/mag97/march97-report.html.
SAMe: The Word Is Out, Life Extension Magazine, Nov. 1999, 2 pgs., http://www.lef.org/magazine/mag99/nov99-products.html.
SAM-E, Whole Health Discount Center Ad printed Dec., 10, 2000, 3 pgs., http://www.health-pages.com/se/.
Spotlight on SAM-e. About.com Web Site, Dec. 15, 1999, 3 pgs., http://www.chronicgatigue.about.com/aa121599a.htm?iam=metacrawl&terms=%2Badenosylmethionin.
Hoe does SAM-e work? Sep. 22, 1999, 2 pgs., http://www.ramonamall.com/How-does-SAM-ework.html.
What is SAM-e. Newsweek online. Jul. 5, 1999, 4 pgs., http://www.ramonamall.com/What-Is-Sam-e.html.
Life Extension Foundation Advertisement for SAMe, printed Dec. 12, 2000, 2 pgs., http://www.lef.org/prod_desc/item00358.html.

* cited by examiner

*Primary Examiner*—Rebecca E. Prouty
*Assistant Examiner*—Malgorzata A. Walicka
(74) *Attorney, Agent, or Firm*—Gardere Wynne Sewell LLP (57) ABSTRACT

The present invention makes use of a chimeric gene that, when incorporated into an appropriate host, results in the overproduction of S-adenosylmethionine without the need to supply the host with a source of untransformed methionine. The need for the methionine source is eliminated because the appropriately chosen host manufactures the amino acid on its own, and when the host is modified by the inclusion of a chimeric gene of the present invention, it transforms the methionine that is produced into S-adenosylmethionine. In addition, the same chimeric gene causes accumulation of methionine and increase in folate content in the same host. One form of the present invention is a fused gene encoding for methylene tetrahydrofolate reductase (MTHFR) made up of an N-terminal domain from a yeast organism and a C-terminal domain from a plant species. An example of a suitable plant species is *Arabidopsis thaliana*. An example of a suitable yeast organism is *Saccharomyces cerevisiae*.

10 Claims, 3 Drawing Sheets

SEQUENCE LISTING

```
<160> NUMBER OF SEQ ID NOS: 13

<210> SEQ ID NO 1
<211> LENGTH: 3082
<212> TYPE: DNA
<213> ORGANISM: Saccharomyces cerevisiae
<220> FEATURE:
<221> NAME/KEY: CDS
<222> LOCATION: (826)..(2625)
<223> OTHER INFORMATION: DNA construct

<400> SEQUENCE: 1
cgggcacgtg ttcttggcca ccttgatgtg catgtttctt ctaggtgagc tacgtgtgtt      60
tgggcgtcgt gcactggctc acttgtacgc gcagaaatgg cagcttgtac gattggtgac     120
ccgccttttc gacactggac cgctatggac gtggcggcgg tgtggcggcg gctcaatgac     180
ctgtggcgcc cgtttgtggc gtgcgatagt cgagccgcct gtcacgtgcg cggccgcccct    240 gctccgtttg acgcgatgca tagcatgcga ccacccagta atcatactgc tgacgctatt     300
ggtcacgtgg ttatggcagc tgctgttgac tgcggtggcg tcccgtttcc acaccgtacg     360
tgagcacatg tctggattgc tagctgcgta catagtgaca ggccttgtct acgctcgcga     420
cgcagccgcg ctacgtccag tatgactcag gaaaagttgg cgatagacca cgagcgactg     480
aaaaaataac agcgactttt ctcccggtag cgggccgtcg tttagtcatt ctatccctcg     540
gattatagac tgtgaatatt gcatatgcaa ctttgactca aatttttcca aaatttgata     600
tatatatata tatatatatg tttgtatgta tatatatata tacgtatata tatcatatat     660
acgaaaagta gaaaaaaaaa ggtgatattt cgctcgtgga aaagctaatg ccacagcttg     720
tgtttcgtgt agtttgcctt gctccccttg attgaaatag tctccctaaa ctaaagttat     780
cagcaaacag aaccaccaca gttactacta caaccacatc gcaat atg aag atc aca     837
                                                    Met Lys Ile Thr
                                                      1 gaa aaa tta gag caa cat aga cag acc tct ggc aag ccc act tac tca       885
Glu Lys Leu Glu Gln His Arg Gln Thr Ser Gly Lys Pro Thr Tyr Ser
 5              10                  15                  20 ttc gag tac ttc gtc ccg aag act aca caa ggt gta cag aac ctg tat       933
Phe Glu Tyr Phe Val Pro Lys Thr Thr Gln Gly Val Gln Asn Leu Tyr
                25                  30                  35 gac cgg atg gac cgg atg tac gag gct tct ttg ccc caa ttt att gac       981
Asp Arg Met Asp Arg Met Tyr Glu Ala Ser Leu Pro Gln Phe Ile Asp
            40                  45                  50 atc acc tgg aat gca ggc ggt gga cgg ttg tca cat ctg tcc acg gac      1029
```

```
Ile Thr Trp Asn Ala Gly Gly Arg Leu Ser His Leu Ser Thr Asp
         55                  60                  65 ttg gtt gcg aca gcg cag tct gtg ctt ggt ttg gaa acg tgc atg cac    1077
Leu Val Ala Thr Ala Gln Ser Val Leu Gly Leu Glu Thr Cys Met His
 70                  75                  80 ctt acc tgc acc aat atg ccc att tcg atg att gac gac gct tta gaa    1125
Leu Thr Cys Thr Asn Met Pro Ile Ser Met Ile Asp Asp Ala Leu Glu
 85                  90                  95                 100 aac gct tat cac tcc ggt tgc cag aac atc cta gcg ctg aga gga gat    1173
Asn Ala Tyr His Ser Gly Cys Gln Asn Ile Leu Ala Leu Arg Gly Asp
                105                 110                 115 cct cct agg gac gca gaa aac tgg act ccc gtt gaa ggt ggc ttc cag    1221
Pro Pro Arg Asp Ala Glu Asn Trp Thr Pro Val Glu Gly Gly Phe Gln
            120                 125                 130 tat gcc aag gac ttg att aag tat atc aag tcc aag tac ggt gac cat    1269
Tyr Ala Lys Asp Leu Ile Lys Tyr Ile Lys Ser Lys Tyr Gly Asp His
        135                 140                 145 ttc gct atc ggc gtt gcc ggc tac ccg gag tgc cat ccg gag ttg cct    1317
Phe Ala Ile Gly Val Ala Gly Tyr Pro Glu Cys His Pro Glu Leu Pro
    150                 155                 160 aac aaa gac gtg aag ctt gat ctc gag tat ttg agc aga aga tcg acc    1365
Asn Lys Asp Val Lys Leu Asp Leu Glu Tyr Leu Ser Arg Arg Ser Thr
165                 170                 175                 180 ggc ggc gac ttc atc atc act cag atg ttt tac gat gtt gat aat tta    1413
Gly Gly Asp Phe Ile Ile Thr Gln Met Phe Tyr Asp Val Asp Asn Leu
                185                 190                 195 ctc aac tgg tgt tcc caa gtt aga gct gcg ggc atg gac gtg ccc att    1461
Leu Asn Trp Cys Ser Gln Val Arg Ala Ala Gly Met Asp Val Pro Ile
            200                 205                 210 att ccc ggg atc atg ccg atc act acc tac gcg gcc ttc ttg aga agg    1509
Ile Pro Gly Ile Met Pro Ile Thr Thr Tyr Ala Ala Phe Leu Arg Arg
        215                 220                 225 atc caa tgg ggc caa atc tcc atc cct caa cat ttc tcg tcc cga ttg    1557
Ile Gln Trp Gly Gln Ile Ser Ile Pro Gln His Phe Ser Ser Arg Leu
    230                 235                 240 gat cct atc aag gac gat gac gag ttg gtc cgt gat atc gga act aac    1605
Asp Pro Ile Lys Asp Asp Asp Glu Leu Val Arg Asp Ile Gly Thr Asn
245                 250                 255                 260 ttg atc gtg gaa atg tgt caa aaa ttg ctc gac agt ggt tac gtt tct    1653
Leu Ile Val Glu Met Cys Gln Lys Leu Leu Asp Ser Gly Tyr Val Ser
                265                 270                 275 cac ttg cac atc tac acc atg aac ttg gaa aaa gcg cct ctc atg att    1701
His Leu His Ile Tyr Thr Met Asn Leu Glu Lys Ala Pro Leu Met Ile
            280                 285                 290 ctg gaa aga ttg aac att cta cct acg gaa tca gag ttc aat gca cat    1749
Leu Glu Arg Leu Asn Ile Leu Pro Thr Glu Ser Glu Phe Asn Ala His
        295                 300                 305 cca ttg gcc gtg ttg cca tgg aga aaa tct ttg aat cca aag cgt aaa    1797
Pro Leu Ala Val Leu Pro Trp Arg Lys Ser Leu Asn Pro Lys Arg Lys
    310                 315                 320 aac gag gaa gtc aga cct atc ttc tgg aag aga aga cct tac tcc tat    1845
Asn Glu Glu Val Arg Pro Ile Phe Trp Lys Arg Arg Pro Tyr Ser Tyr
325                 330                 335                 340 gtc gca aga acc tct caa tgg gcc gtg gac gaa ttc ccc aac ggt aga    1893
Val Ala Arg Thr Ser Gln Trp Ala Val Asp Glu Phe Pro Asn Gly Arg
                345                 350                 355 ttc ggt gat tcg tct tct cct gcg ttc ggt gac ttg gat ctg tgt ggt    1941
Phe Gly Asp Ser Ser Ser Pro Ala Phe Gly Asp Leu Asp Leu Cys Gly
            360                 365                 370
```

-continued

| | | |
|---|---|---|
| tca gac ttg atc agg caa tca gcg aac aaa tgt ctc gaa tta tgg tcc<br>Ser Asp Leu Ile Arg Gln Ser Ala Asn Lys Cys Leu Glu Leu Trp Ser<br>     375                   380                   385 | 1989 | acc cct act tcc atc aac gac gtc gcc ttc ttg gtc atc aac tac ttg   2037
Thr Pro Thr Ser Ile Asn Asp Val Ala Phe Leu Val Ile Asn Tyr Leu
      390                 395                 400 aat gga aac ttg aag tgt tta cct tgg agt gat atc ccc atc aat gat   2085
Asn Gly Asn Leu Lys Cys Leu Pro Trp Ser Asp Ile Pro Ile Asn Asp
405                 410                 415                 420 gaa ata aat cca atc aaa gca cac ttg att gag ctg aac cag cat tct   2133
Glu Ile Asn Pro Ile Lys Ala His Leu Ile Glu Leu Asn Gln His Ser
                425                 430                 435 atc atc act ata aac tct caa cct caa gtc aac ggc att agg tcc aat   2181
Ile Ile Thr Ile Asn Ser Gln Pro Gln Val Asn Gly Ile Arg Ser Asn
            440                 445                 450 gac aaa att cat ggt tgg gga ccc aag gat ggt tac gtt tac cag aag   2229
Asp Lys Ile His Gly Trp Gly Pro Lys Asp Gly Tyr Val Tyr Gln Lys
        455                 460                 465 caa tat ttg gaa ttt atg ttg ccc aag act aag ttg ccc aag ttg att   2277
Gln Tyr Leu Glu Phe Met Leu Pro Lys Thr Lys Leu Pro Lys Leu Ile
    470                 475                 480 gac acc ttg aaa aac aat gag ttc ttg acc tac ttc gcc atc gac tct   2325
Asp Thr Leu Lys Asn Asn Glu Phe Leu Thr Tyr Phe Ala Ile Asp Ser
485                 490                 495                 500 caa ggt gac ctg cta agt aat cat cca gac aac tcc aag tcc aac gct   2373
Gln Gly Asp Leu Leu Ser Asn His Pro Asp Asn Ser Lys Ser Asn Ala
                505                 510                 515 gtg act tgg ggt att ttc ccc ggc aga gaa att ctt caa cct acc att   2421
Val Thr Trp Gly Ile Phe Pro Gly Arg Glu Ile Leu Gln Pro Thr Ile
            520                 525                 530 gtc gag aaa att tcg ttc tta gcg tgg aag gag gag ttc tat cat atc   2469
Val Glu Lys Ile Ser Phe Leu Ala Trp Lys Glu Glu Phe Tyr His Ile
        535                 540                 545 ttg aat gaa tgg aaa cta aac atg aat aaa tac gat aaa ccg cat agt   2517
Leu Asn Glu Trp Lys Leu Asn Met Asn Lys Tyr Asp Lys Pro His Ser
    550                 555                 560 gcc caa ttc att cag tcc ttg att gac gat tac tgc ttg gtc aat att   2565
Ala Gln Phe Ile Gln Ser Leu Ile Asp Asp Tyr Cys Leu Val Asn Ile
565                 570                 575                 580 gtt gac aat gac tac att tct cca gat gat caa atc cat tcc atc cta   2613
Val Asp Asn Asp Tyr Ile Ser Pro Asp Asp Gln Ile His Ser Ile Leu
                585                 590                 595 cta agc cta taa taacacagac aacgataaca gttctttaac agaattgtca        2665
Leu Ser Leu acccccctc tttgcattac attcaacatt acattgcatt ttttttttt tattcactat    2725 tattatggtt cttctttttt accagatttt gctccttcct tttccattgt tttaccattc  2785 tttttaact agcatttcaa catgtgtttg gttaacaccc cttcttttt ttcaggaaaa    2845 tcctttcatt tcttctcata ctttcaacaa agttttttaa aggtacttta aaatagttca  2905
acaccctctt ccttcattta tttattctct tcatattcaa catactcgaa aaggaagaac  2965
actaaaagta cttacatttt cacatgtatg tatacctata tatatatata tatatactct  3025
tatagatata tttacaaatt aaaggaaaaa ataataaaat aacctccctg tcacaag     3082

<210> SEQ ID NO 2
<211> LENGTH: 599
<212> TYPE: PRT
<213> ORGANISM: Saccharomyces cerevisiae

<400> SEQUENCE: 2

```
Met Lys Ile Thr Glu Lys Leu Glu Gln His Arg Gln Thr Ser Gly Lys
1               5                   10                  15

Pro Thr Tyr Ser Phe Glu Tyr Phe Val Pro Lys Thr Thr Gln Gly Val
            20                  25                  30

Gln Asn Leu Tyr Asp Arg Met Asp Arg Met Tyr Glu Ala Ser Leu Pro
        35                  40                  45

Gln Phe Ile Asp Ile Thr Trp Asn Ala Gly Gly Arg Leu Ser His
    50                  55                  60

Leu Ser Thr Asp Leu Val Ala Thr Ala Gln Ser Val Leu Gly Leu Glu
65                  70                  75                  80

Thr Cys Met His Leu Thr Cys Thr Asn Met Pro Ile Ser Met Ile Asp
                85                  90                  95

Asp Ala Leu Glu Asn Ala Tyr His Ser Gly Cys Gln Asn Ile Leu Ala
                100                 105                 110

Leu Arg Gly Asp Pro Pro Arg Asp Ala Glu Asn Trp Thr Pro Val Glu
            115                 120                 125

Gly Gly Phe Gln Tyr Ala Lys Asp Leu Ile Lys Tyr Ile Lys Ser Lys
    130                 135                 140

Tyr Gly Asp His Phe Ala Ile Gly Val Ala Gly Tyr Pro Glu Cys His
145                 150                 155                 160

Pro Glu Leu Pro Asn Lys Asp Val Lys Leu Asp Leu Glu Tyr Leu Ser
                165                 170                 175

Arg Arg Ser Thr Gly Gly Asp Phe Ile Ile Thr Gln Met Phe Tyr Asp
            180                 185                 190

Val Asp Asn Leu Leu Asn Trp Cys Ser Gln Val Arg Ala Ala Gly Met
    195                 200                 205

Asp Val Pro Ile Ile Pro Gly Ile Met Pro Ile Thr Thr Tyr Ala Ala
210                 215                 220

Phe Leu Arg Arg Ile Gln Trp Gly Gln Ile Ser Ile Pro Gln His Phe
225                 230                 235                 240

Ser Ser Arg Leu Asp Pro Ile Lys Asp Asp Glu Leu Val Arg Asp
                245                 250                 255

Ile Gly Thr Asn Leu Ile Val Glu Met Cys Gln Lys Leu Leu Asp Ser
            260                 265                 270

Gly Tyr Val Ser His Leu His Ile Tyr Thr Met Asn Leu Glu Lys Ala
    275                 280                 285

Pro Leu Met Ile Leu Glu Arg Leu Asn Ile Leu Pro Thr Glu Ser Glu
290                 295                 300

Phe Asn Ala His Pro Leu Ala Val Leu Pro Trp Arg Lys Ser Leu Asn
305                 310                 315                 320

Pro Lys Arg Lys Asn Glu Glu Val Arg Pro Ile Phe Trp Lys Arg Arg
                325                 330                 335

Pro Tyr Ser Tyr Val Ala Arg Thr Ser Gln Trp Ala Val Asp Glu Phe
            340                 345                 350

Pro Asn Gly Arg Phe Gly Asp Ser Ser Pro Ala Phe Gly Asp Leu
    355                 360                 365

Asp Leu Cys Gly Ser Asp Leu Ile Arg Gln Ser Ala Asn Lys Cys Leu
370                 375                 380

Glu Leu Trp Ser Thr Pro Thr Ser Ile Asn Asp Val Ala Phe Leu Val
385                 390                 395                 400

Ile Asn Tyr Leu Asn Gly Asn Leu Lys Cys Leu Pro Trp Ser Asp Ile
            405                 410                 415
```

```
Pro Ile Asn Asp Glu Ile Asn Pro Ile Lys Ala His Leu Ile Glu Leu
        420                 425                 430

Asn Gln His Ser Ile Ile Thr Ile Asn Ser Gln Pro Gln Val Asn Gly
            435                 440                 445

Ile Arg Ser Asn Asp Lys Ile His Gly Trp Gly Pro Lys Asp Gly Tyr
        450                 455                 460

Val Tyr Gln Lys Gln Tyr Leu Glu Phe Met Leu Pro Lys Thr Lys Leu
465                 470                 475                 480

Pro Lys Leu Ile Asp Thr Leu Lys Asn Asn Glu Phe Leu Thr Tyr Phe
                485                 490                 495

Ala Ile Asp Ser Gln Gly Asp Leu Leu Ser Asn His Pro Asp Asn Ser
            500                 505                 510

Lys Ser Asn Ala Val Thr Trp Gly Ile Phe Pro Gly Arg Glu Ile Leu
        515                 520                 525

Gln Pro Thr Ile Val Glu Lys Ile Ser Phe Leu Ala Trp Lys Glu Glu
    530                 535                 540

Phe Tyr His Ile Leu Asn Glu Trp Lys Leu Asn Met Asn Lys Tyr Asp
545                 550                 555                 560

Lys Pro His Ser Ala Gln Phe Ile Gln Ser Leu Ile Asp Asp Tyr Cys
                565                 570                 575

Leu Val Asn Ile Val Asp Asn Asp Tyr Ile Ser Pro Asp Gln Ile
            580                 585                 590

His Ser Ile Leu Leu Ser Leu
        595

<210> SEQ ID NO 3
<211> LENGTH: 1994
<212> TYPE: DNA
<213> ORGANISM: Arabidopsis thaliana
<220> FEATURE:
<221> NAME/KEY: CDS
<222> LOCATION: (63)..(1841)
<223> OTHER INFORMATION: DNA construct

<400> SEQUENCE: 3
acttcctcta cctatctaat tccgaatctg gatttggatt tggatctcat ttcgattcaa      60 cg atg aag gtg gtt gat aag atc aaa tcc gtg acg gag caa ggc caa      107
   Met Lys Val Val Asp Lys Ile Lys Ser Val Thr Glu Gln Gly Gln
   1               5                   10                  15 aca gct ttc tcc ttc gag ttt ttc cca ccg aag aca gaa gat ggc gtc      155
Thr Ala Phe Ser Phe Glu Phe Phe Pro Pro Lys Thr Glu Asp Gly Val
                20                  25                  30 gag aat ctc ttt gaa cga atg gat cga ttg gtc tct tat gga cct acc      203
Glu Asn Leu Phe Glu Arg Met Asp Arg Leu Val Ser Tyr Gly Pro Thr
            35                  40                  45 ttc tgc gat atc act tgg ggt gct ggt gga tcc aca gct gat ctc act      251
Phe Cys Asp Ile Thr Trp Gly Ala Gly Gly Ser Thr Ala Asp Leu Thr
        50                  55                  60 ctc gag att gct tct agg atg cag aat gtt atc tgc gtc gag act atg      299
Leu Glu Ile Ala Ser Arg Met Gln Asn Val Ile Cys Val Glu Thr Met
65                  70                  75 atg cat ctc act tgt acc aac atg ccg att gag aag att gat cac gcg      347
Met His Leu Thr Cys Thr Asn Met Pro Ile Glu Lys Ile Asp His Ala
80                  85                  90                  95 ctt gag acg att aga tct aat gga att cag aat gtg ctt gct ctt aga      395
Leu Glu Thr Ile Arg Ser Asn Gly Ile Gln Asn Val Leu Ala Leu Arg
                100                 105                 110
```

-continued

```
gga gat cct cct cat gga caa gat aag ttt gtt cag gtt gaa gga gga    443
Gly Asp Pro Pro His Gly Gln Asp Lys Phe Val Gln Val Glu Gly Gly
            115                 120                 125 ttt gct tgt gct ttg gat ctg gtg aat cac att cgt agc aag tat ggt    491
Phe Ala Cys Ala Leu Asp Leu Val Asn His Ile Arg Ser Lys Tyr Gly
        130                 135                 140 gat tac ttt gga atc act gtt gct ggt tat cct gag gct cat ccg gat    539
Asp Tyr Phe Gly Ile Thr Val Ala Gly Tyr Pro Glu Ala His Pro Asp
    145                 150                 155 gtt att gaa gct gat gga ctt gct act cct gaa tct tat cag agt gat    587
Val Ile Glu Ala Asp Gly Leu Ala Thr Pro Glu Ser Tyr Gln Ser Asp
160                 165                 170                 175 ctt gct tac ttg aag aaa aag gtt gat gct gga gca gat ttg att gtg    635
Leu Ala Tyr Leu Lys Lys Lys Val Asp Ala Gly Ala Asp Leu Ile Val
                180                 185                 190 act cag ctt ttc tat gat act gat ata ttc ctc aag ttt gtg aat gat    683
Thr Gln Leu Phe Tyr Asp Thr Asp Ile Phe Leu Lys Phe Val Asn Asp
            195                 200                 205 tgt cgg caa atc ggg att aat tgt ccc att gtt cct gga att atg cct    731
Cys Arg Gln Ile Gly Ile Asn Cys Pro Ile Val Pro Gly Ile Met Pro
        210                 215                 220 att tcc aac tac aag ggg ttc ttg cgt atg gct ggt ttc tgt aag acc    779
Ile Ser Asn Tyr Lys Gly Phe Leu Arg Met Ala Gly Phe Cys Lys Thr
    225                 230                 235 aag ata ccc gct gag ctc act gct gcc tta gag cct att aag gat aat    827
Lys Ile Pro Ala Glu Leu Thr Ala Ala Leu Glu Pro Ile Lys Asp Asn
240                 245                 250                 255 gac gag gct gtt aaa gcc tat gga att cac ttt gca aca gaa atg tgc    875
Asp Glu Ala Val Lys Ala Tyr Gly Ile His Phe Ala Thr Glu Met Cys
                260                 265                 270 aaa aag att ttg gcc cat gga atc act tcc ctt cat ctc tac aca ttg    923
Lys Lys Ile Leu Ala His Gly Ile Thr Ser Leu His Leu Tyr Thr Leu
            275                 280                 285 aac gtg gac aaa tca gct att ggg ata tta atg aac ctt ggt ctg att    971
Asn Val Asp Lys Ser Ala Ile Gly Ile Leu Met Asn Leu Gly Leu Ile
        290                 295                 300 gat gag tca aaa att tct cgt tct cta cct tgg aga cgc cct gca aat   1019
Asp Glu Ser Lys Ile Ser Arg Ser Leu Pro Trp Arg Arg Pro Ala Asn
    305                 310                 315 gtt ttc cgt act aag gaa gat gtt cgc cca att ttc tgg gca aac cgt   1067
Val Phe Arg Thr Lys Glu Asp Val Arg Pro Ile Phe Trp Ala Asn Arg
320                 325                 330                 335 cca aag agc tac ata tct aga aca aag ggc tgg aat gac ttc cca cat   1115
Pro Lys Ser Tyr Ile Ser Arg Thr Lys Gly Trp Asn Asp Phe Pro His
                340                 345                 350 gga cgt tgg ggt gat tca cac agt gca gca tac agt aca ctt tcg gat   1163
Gly Arg Trp Gly Asp Ser His Ser Ala Ala Tyr Ser Thr Leu Ser Asp
            355                 360                 365 tat cag ttt gcg cgc cca aaa gga cgt gac aag aag ctt cag caa gaa   1211
Tyr Gln Phe Ala Arg Pro Lys Gly Arg Asp Lys Lys Leu Gln Gln Glu
        370                 375                 380 tgg gtc gtc cca ctg aaa agc att gaa gat gtt caa gag aaa ttc aaa   1259
Trp Val Val Pro Leu Lys Ser Ile Glu Asp Val Gln Glu Lys Phe Lys
    385                 390                 395 gag ctc tgc att gga aac tta aaa agc agc cca tgg tct gaa tta gat   1307
Glu Leu Cys Ile Gly Asn Leu Lys Ser Ser Pro Trp Ser Glu Leu Asp
400                 405                 410                 415 gga ctc cag cca gag aca aag atc ata aat gag caa ctc gga aaa atc   1355
Gly Leu Gln Pro Glu Thr Lys Ile Ile Asn Glu Gln Leu Gly Lys Ile
                420                 425                 430
```

```
aac tcc aac ggt ttc ctg acc att aat agc caa cca tca gtc aat gca    1403
Asn Ser Asn Gly Phe Leu Thr Ile Asn Ser Gln Pro Ser Val Asn Ala
            435                 440                 445 gcc aaa tcc gat tct cca gct att gga tgg ggt ggt cct ggt ggt tac    1451
Ala Lys Ser Asp Ser Pro Ala Ile Gly Trp Gly Gly Pro Gly Gly Tyr
        450                 455                 460 gtc tac cag aaa gct tat ctg gag ttc ttc tgt tca aag gat aag tta    1499
Val Tyr Gln Lys Ala Tyr Leu Glu Phe Phe Cys Ser Lys Asp Lys Leu
    465                 470                 475 gac aca ctt gtg gag aaa tcc aaa gct ttt cct tct atc acc tac atg    1547
Asp Thr Leu Val Glu Lys Ser Lys Ala Phe Pro Ser Ile Thr Tyr Met
480                 485                 490                 495 gcc gtg aac aaa tca gag aat tgg gta tca aac acc ggt gag tcc gat    1595
Ala Val Asn Lys Ser Glu Asn Trp Val Ser Asn Thr Gly Glu Ser Asp
                500                 505                 510 gtg aat gca gtt act tgg gga gtg ttc cca gct aag gag gtt att caa    1643
Val Asn Ala Val Thr Trp Gly Val Phe Pro Ala Lys Glu Val Ile Gln
            515                 520                 525 ccg acg atc gtg gat cca gcc agt ttc aaa gtc tgg aaa gac gaa gcg    1691
Pro Thr Ile Val Asp Pro Ala Ser Phe Lys Val Trp Lys Asp Glu Ala
        530                 535                 540 ttt gag att tgg tca aga agc tgg gct aac ttg tac cca gaa gat gac    1739
Phe Glu Ile Trp Ser Arg Ser Trp Ala Asn Leu Tyr Pro Glu Asp Asp
545                 550                 555 cct tct aga aag ttg ctc gag gag gtg aag aac agc tac tat ttg gta    1787
Pro Ser Arg Lys Leu Leu Glu Glu Val Lys Asn Ser Tyr Tyr Leu Val
560                 565                 570                 575 agc tta gtg gac aac aat tac atc aat ggt gat atc ttc tct gtc ttt    1835
Ser Leu Val Asp Asn Asn Tyr Ile Asn Gly Asp Ile Phe Ser Val Phe
                580                 585                 590 gct tga tctccgagaa aaccaccggc gaagaggaaa cattcgattt cgagatttgt    1891
Ala tttgtacctt ttaaagttat ttttgattcg taataacctt actttgatga atcaacaaaa    1951
acatcagttt gattgcaatg aaaaaaatcg ccttagcggt ttg                      1994

<210> SEQ ID NO 4
<211> LENGTH: 592
<212> TYPE: PRT
<213> ORGANISM: Arabidopsis thaliana

<400> SEQUENCE: 4

Met Lys Val Val Asp Lys Ile Lys Ser Val Thr Glu Gln Gly Gln Thr
1               5                   10                  15

Ala Phe Ser Phe Glu Phe Phe Pro Pro Lys Thr Glu Asp Gly Val Glu
            20                  25                  30

Asn Leu Phe Glu Arg Met Asp Arg Leu Val Ser Tyr Gly Pro Thr Phe
        35                  40                  45

Cys Asp Ile Thr Trp Gly Ala Gly Gly Ser Thr Ala Asp Leu Thr Leu
    50                  55                  60

Glu Ile Ala Ser Arg Met Gln Asn Val Ile Cys Val Glu Thr Met Met
65                  70                  75                  80

His Leu Thr Cys Thr Asn Met Pro Ile Glu Lys Ile Asp His Ala Leu
                85                  90                  95

Glu Thr Ile Arg Ser Asn Gly Ile Gln Asn Val Leu Ala Leu Arg Gly
            100                 105                 110

Asp Pro Pro His Gly Gln Asp Lys Phe Val Gln Val Glu Gly Gly Phe
        115                 120                 125
```

```
Ala Cys Ala Leu Asp Leu Val Asn His Ile Arg Ser Lys Tyr Gly Asp
    130                 135                 140
Tyr Phe Gly Ile Thr Val Ala Gly Tyr Pro Glu Ala His Pro Asp Val
145                 150                 155                 160
Ile Glu Ala Asp Gly Leu Ala Thr Pro Glu Ser Tyr Gln Ser Asp Leu
                165                 170                 175
Ala Tyr Leu Lys Lys Val Asp Ala Gly Ala Asp Leu Ile Val Thr
            180                 185                 190
Gln Leu Phe Tyr Asp Thr Asp Ile Phe Leu Lys Phe Val Asn Asp Cys
        195                 200                 205
Arg Gln Ile Gly Ile Asn Cys Pro Ile Val Pro Gly Ile Met Pro Ile
    210                 215                 220
Ser Asn Tyr Lys Gly Phe Leu Arg Met Ala Gly Phe Cys Lys Thr Lys
225                 230                 235                 240
Ile Pro Ala Glu Leu Thr Ala Ala Leu Glu Pro Ile Lys Asp Asn Asp
                245                 250                 255
Glu Ala Val Lys Ala Tyr Gly Ile His Phe Ala Thr Glu Met Cys Lys
            260                 265                 270
Lys Ile Leu Ala His Gly Ile Thr Ser Leu His Leu Tyr Thr Leu Asn
        275                 280                 285
Val Asp Lys Ser Ala Ile Gly Ile Leu Met Asn Leu Gly Leu Ile Asp
    290                 295                 300
Glu Ser Lys Ile Ser Arg Ser Leu Pro Trp Arg Arg Pro Ala Asn Val
305                 310                 315                 320
Phe Arg Thr Lys Glu Asp Val Arg Pro Ile Phe Trp Ala Asn Arg Pro
                325                 330                 335
Lys Ser Tyr Ile Ser Arg Thr Lys Gly Trp Asn Asp Phe Pro His Gly
            340                 345                 350
Arg Trp Gly Asp Ser His Ser Ala Ala Tyr Ser Thr Leu Ser Asp Tyr
        355                 360                 365
Gln Phe Ala Arg Pro Lys Gly Arg Asp Lys Lys Leu Gln Gln Glu Trp
    370                 375                 380
Val Val Pro Leu Lys Ser Ile Glu Asp Val Gln Glu Lys Phe Lys Glu
385                 390                 395                 400
Leu Cys Ile Gly Asn Leu Lys Ser Ser Pro Trp Ser Glu Leu Asp Gly
                405                 410                 415
Leu Gln Pro Glu Thr Lys Ile Ile Asn Glu Gln Leu Gly Lys Ile Asn
            420                 425                 430
Ser Asn Gly Phe Leu Thr Ile Asn Ser Gln Pro Ser Val Asn Ala Ala
        435                 440                 445
Lys Ser Asp Ser Pro Ala Ile Gly Trp Gly Pro Gly Gly Tyr Val
    450                 455                 460
Tyr Gln Lys Ala Tyr Leu Glu Phe Phe Cys Ser Lys Asp Lys Leu Asp
465                 470                 475                 480
Thr Leu Val Glu Lys Ser Lys Ala Phe Pro Ser Ile Thr Tyr Met Ala
                485                 490                 495
Val Asn Lys Ser Glu Asn Trp Val Ser Asn Thr Gly Glu Ser Asp Val
            500                 505                 510
Asn Ala Val Thr Trp Gly Val Phe Pro Ala Lys Glu Val Ile Gln Pro
        515                 520                 525
Thr Ile Val Asp Pro Ala Ser Phe Lys Val Trp Lys Asp Glu Ala Phe
    530                 535                 540
```

```
Glu Ile Trp Ser Arg Ser Trp Ala Asn Leu Tyr Pro Glu Asp Pro
545                 550                 555                 560

Ser Arg Lys Leu Leu Glu Glu Val Lys Asn Ser Tyr Tyr Leu Val Ser
            565                 570                 575

Leu Val Asp Asn Asn Tyr Ile Asn Gly Asp Ile Phe Ser Val Phe Ala
        580                 585                 590
```

```
<210> SEQ ID NO 5
<211> LENGTH: 26
<212> TYPE: DNA
<213> ORGANISM: Saccharomyces cerevisiae

<400> SEQUENCE: 5
catgaagatc acagaaaaat tagagc                                      26

<210> SEQ ID NO 6
<211> LENGTH: 29
<212> TYPE: DNA
<213> ORGANISM: Saccharomyces cerevisiae

<400> SEQUENCE: 6
ggtttgccca agagataggt ctgacttcc                                   29

<210> SEQ ID NO 7
<211> LENGTH: 30
<212> TYPE: DNA
<213> ORGANISM: Arabidopsis thaliana

<400> SEQUENCE: 7
cctatcttct gggcaaaccg tccaaagagc                                  30

<210> SEQ ID NO 8
<211> LENGTH: 29
<212> TYPE: DNA
<213> ORGANISM: Arabidopsis thaliana

<400> SEQUENCE: 8
tgcactgcag tcaagcaaag acagagaag                                   29

<210> SEQ ID NO 9
<211> LENGTH: 20
<212> TYPE: DNA
<213> ORGANISM: CHIMERA1

<400> SEQUENCE: 9
caacaggttc atgccactgg                                             20

<210> SEQ ID NO 10
<211> LENGTH: 52
<212> TYPE: DNA
<213> ORGANISM: CHIMERA1

<400> SEQUENCE: 10
acaatggaaa aggaaggagc aaaatctggt aaaaattctc ggagatcaag ca         52

<210> SEQ ID NO 11
<211> LENGTH: 21
<212> TYPE: DNA
<213> ORGANISM: CHIMERA1

<400> SEQUENCE: 11
aaggtgatat ttcgctcgtg g                                           21
```

```
<210> SEQ ID NO 12
<211> LENGTH: 21
<212> TYPE: DNA
<213> ORGANISM: CHIMERA1

<400> SEQUENCE: 12
atggatccgg gtgttaacca a                                              21

<210> SEQ ID NO 13
<211> LENGTH: 42
<212> TYPE: DNA
<213> ORGANISM: CHIMERA1

<400> SEQUENCE: 13
gaagtcagac ctatcttctg ggcaaaccgt ccaaagagct ac                       42
```

BIOSYNTHESIS OF S-ADENOSYLMETHIONINE IN A RECOMBINANT YEAST STRAIN

FIELD OF THE INVENTION

This Application claims the benefit of U.S. Provisional Application No. 60/280,333, filed Mar. 30, 2001.

The U.S. Government may own certain rights in this invention pursuant to the terms of the National Science Foundation grant INB-9813999 and the National Institutes of Health grant RR09276.

BACKGROUND OF THE INVENTION

The present invention relates in general to the field of recombinant DNA species, and more particularly to the production of chimeric genes.

S-adenosylmethionine is an important metabolic agent that is formed in the body by the reaction of methionine, an essential amino acid, with adenosine triphosphate (ATP). S-adenosylmethionine is active in more than forty biological reactions in vivo. S-adenosylmethionine also operates in association with folic acid and vitamin B-12 as a methylating agent, and is essential for the formation of many sulfur-containing compounds in the body, including glutathione and various components of cartilaginous connective tissue.

The body normally generates the required level of S-adenosylmethionine directly from the amino acid methionine; however, a deficiency of methionine, folic acid, or vitamin B-12 can result in decreased levels of S-adenosylmethionine. There is interest in the effects of supplemental dosages of S-adenosylmethionine on various conditions. The interest in supplementation stems, in part, from findings that the elderly and those suffering from osteoarthritis, various liver problems, and depression typically have lowered levels of S-adenosylmethionine. It is also known that merely increasing the dietary intake of methionine does not result in an increase in the concentration of S-adenosylmethionine in the body. S-adenosylmethionine is now widely distributed as an over-the-counter dietary supplement.

S-adenosylmethionine is primarily used in the treatment of five conditions: depression, osteoarthritis, fibromyalgia, cirrhosis of the liver and migraine headaches. There have been numerous studies that have supported the efficacy of S-adenosylmethionine for the treatment of these conditions. It has also been recognized that S-adenosylmethionine has an excellent safety record, and is therefore appropriate for long-term use by patients.

A major drawback to the use of S-adenosylmethionine as a medicament is the expense. Present methods of production rely on the modification of methionine. Unfortunately, the purified methionine used as a starting material is relatively expensive. There is therefore a need for a method of production of S-adenosylmethionine that eliminates the need to provide a source of methionine.

SUMMARY OF THE INVENTION

The present invention makes use of a chimeric or "fused" gene that, when incorporated into an appropriate host, results in the overproduction of S-adenosylmethionine without the need to supply the host with a source of untransformed methionine. The need for the methionine source is eliminated by virtue of the fact that the appropriately chosen host manufactures the amino acid on its own, and when the host is modified by the inclusion of a chimeric gene of the present invention, it transforms the methionine that is produced into S-adenosylmethionine.

One form of the present invention is a fused gene encoding for methylene tetrahydrofolate reductase (MTHFR) made up of an N-terminal domain from a yeast organism and a C-terminal domain from a plant species. An example of a suitable plant species is *Arabidopsis thaliana*. An example of a suitable yeast organism is *Saccharomyces cerevisiae*.

Other forms of the present invention includes a recombinant DNA vector that includes the fused gene referred to above and host cells, both prokaryotic and eukaryotic, that contain the recombinant DNA vector. The present invention may also take the form of a plasmid containing the fused gene referred to above.

Another form of the present invention is a nucleic acid sequence of at least 14 nucleotides from the region where the two domains are joined to form the chimeric gene. Yet another form of the present invention is a purified fusion protein encoded for by the gene referred to above.

And yet another form of the present invention includes a recombinant DNA vector that includes the fused gene referred to above and host cells, both prokaryotic and eukaryotic, animal, yeast, or plant, that contain the recombinant DNA vector wherein the fused gene modifies methylneogenesis. The present invention may also take the form of a plasmid containing the fused gene referred to above.

BRIEF DESCRIPTION OF THE DRAWINGS

The above and further advantages of the invention may be better understood by referring to the following description in conjunction with the accompanying figures in which.

DETAILED DESCRIPTION OF THE INVENTION

While the making and using of various embodiments of the present invention are discussed herein in terms of recombinant yeasts and a method of producing them, it should be appreciated that the present invention provides many applicable inventive concepts that can be embodied in a wide variety of specific contexts. The specific embodiments discussed herein are merely illustrative of specific ways to make and use the invention and are not meant to limit the scope of the invention in any way.

Definitions

Terms used herein have meanings as commonly understood by a person of ordinary skill in the areas relevant to the present invention. Terms such as "a," "an," and "the" are not intended to refer to only a singular entity, but include the general class of which a specific example may be used for illustration. The terminology herein is used to describe specific embodiments of the invention, but their usage does not limit the invention, except as outlined in the claims.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid having an open reading frame encoding a polypeptide, such as a polypeptide, including both exon and (optionally) intron sequences. In yet another embodiment, the nucleic acid is DNA or RNA.

The term "fused gene" and "chimeric gene" are used interchangeably, and refer to a functional gene that has a regulatory domain from one organism and the catalytic domain from another, that have been spliced together using recombinant DNA techniques. The two domains may be attached directly to one another, or they may be connected using intervening nucleic acid sequences. The term "intervening nucleic acid sequences" means any segment of DNA used to connect the two domains that make up the "fused gene."

"Domain" refers to a discreet region of a protein that performs a specific function. "N-terminal domain" and "C-terminal domain" refer to the relative end of the protein that is ultimately produced by the expression of a gene. "C" and "N" refer to the carboxyl and amino terminal ends of the protein, respectively.

"Regulatory sequences" of nucleic acids is a generic term used throughout the specification to refer to DNA sequences, such as initiation signals, enhancers, and promoters, as well as polyadenylation sites, which induce or control transcription of protein coding sequences with which they are operably linked. In some embodiments, transcription of a recombinant gene is under the control of a promoter sequence (or other transcriptional regulatory sequence) that controls the expression of the recombinant gene in a cell-type in which expression is intended. It will also be understood that the recombinant gene can be under the control of transcriptional regulatory sequences that are the same or which are different from those sequences and which control transcription of the naturally occurring form of the gene.

When referring to proteins, "regulatory domains" are the portion of a protein that controls the activity of the catalytic domain of that protein. In the present invention, the regulatory domain is the sequence that controls the activity of methylene tetrahydrofolate reductase.

"Catalytic domain" refers to DNA sequences that ultimately encode for amino acid sequences that form an enzymatically active protein. In the present case, that is the DNA sequence that ultimately encodes methylene tetrahydrofolate reductase. When referring to a protein, a "catalytic domain" is the portion of the protein that produces the enzymatic activity associated with the protein.

"Cells" or "cell cultures" or "recombinant host cells" or "host cells" are often used interchangeably as will be clear from the context. These terms include the immediate subject cell which expresses, e.g., the methylene tetrahydrofolate reductase encoded for by the fused gene of the present invention. It is understood that not all progeny are exactly identical to the parental cell, due to chance mutations or difference in environment. Such altered progeny are included in these terms, so long as the progeny retain the characteristics relevant to those conferred on the originally transformed cell.

As used herein, the term "vector" refers to a nucleic acid molecule capable of transporting another nucleic acid to which it has been linked. The term "expression vector" includes DNA expression constructs, e.g., nucleic acid segments, plasmids, cosmids, phages, viruses or virus particles capable of synthesizing the subject proteins encoded by their respective recombinant genes carried by the vector. Alternatively, nucleic acid segments may also be used to create transgenic cells using non-directional or even homologous recombination. Vectors for use with the invention are those capable of autonomous replication and/or expression of nucleic acids to which they are linked. In the present specification, "plasmid" and "vector" are used interchangeably as the plasmid is the most commonly used form of a vector. Moreover, the invention is intended to include such other forms of expression vectors that serve equivalent functions and which become known in the art subsequently hereto.

"Homology" and "identity" each refer to sequence similarity between two polypeptide sequences, with identity being a more strict comparison. Homology and identity can each be determined by comparing a position in each sequence that may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position.

A percentage of homology or identity between sequences is a function of the number of matching or homologous positions shared by the sequences. An "unrelated" or "non-homologous" sequence shares less than 40 percent identity, though it may be less than 25 percent identity, with a reference sequence. An "unrelated" or "non-homologous" sequence can also be referred to as not being "substantially homologous" to the reference sequence. The terms "homology" and "similarity" are used interchangeably herein.

By "purified", it is meant, when referring to the component proteins preparations used to generate the reconstituted protein mixture, that the indicated molecule is present in the substantial absence of other biological macromolecules, such as other proteins (particularly other proteins that may substantially mask, diminish, confuse or alter the characteristics of the component proteins either as purified preparations or in their function in the subject reconstituted mixture).

The term "purified" as used herein preferably means at least 80% by dry weight, 95-99% by weight or even 99.8% by weight, of biological macromolecules of the same type present (but water, buffers, and other small molecules, especially molecules having a molecular weight of less than 5000, may be present). The term "pure" as used herein preferably has the same numerical limits as "purified" immediately above. "Isolated" and "purified" do not encompass either protein in its native state (e.g., as a part of a cell), or as part of a cell lysate, or that have been separated into components (e.g., in an acrylamide gel) but not obtained either as pure (e.g., lacking contaminating proteins) substances or solutions.

The term "isolated" as used herein may also refer to a component protein that is substantially free of cellular material or culture medium when produced by recombinant DNA techniques, or chemical precursors or other chemicals when chemically synthesized.

The term "recombinant protein" refers to a protein that is produced by recombinant DNA techniques, wherein generally DNA encoding the protein is inserted into a suitable expression vector that is in turn used to transform a host cell to produce the heterologous protein. Moreover, the phrase "derived from", with respect to a recombinant gene, is meant to include within the meaning of "recombinant protein" those proteins having an amino acid sequence corresponding to a naturally occurring protein or an amino acid sequence similar thereto that is generated by mutations including substitutions and deletions.

All technical and scientific terms used herein have the same meaning as commonly understood by one of ordinary skill in the art to which this invention belongs, unless defined otherwise. Methods and materials similar or equivalent to those described herein may be used in the practice or testing of the present invention, the generally used methods and materials are now described.

Inserting Chimeric Genes into Plant Cells

A variety of methods may be used to insert foreign DNA, e.g., the chimeric genes of the present invention into plant cells. One such method, involves inserting a chimeric gene into Ti plasmids carried by *A. tumefaciens*, and co-cultivating the *A. tumefaciens* cells with plants. In this process, a segment of T-DNA carrying the chimeric gene is transferred into the plant genome, causing transformation.

A variety of other methods are listed below. These methods are capable of inserting the chimeric genes of this invention into plant cells, although the reported transformation efficiencies achieved to date by such methods have been low. The chimeric genes of this invention (especially those chimeric genes such as neomycin phosphotransferase I and II, NPTI and NPTII, respectively, which may be used as selectable markers because the gene codes for the aminoglycoside 3'-phosphotransferase enzyme that inactivates by phosphorylation a range of aminoglycoside antibiotics) are likely to facilitate research on methods of inserting DNA into plants or plant cells.

While only relatively small DNA molecules have been transferred into plant cells by means of liposomes, and none have yet been expressed, future, liposome-delivery technology may be developed, to transfer plasmids containing the chimeric genes of this invention into plant cells by means involving liposomes. Another technique involves contacting plant cells with vector DNA that is complexed with either (a) polycationic substances, such as poly-L-ornithine, or (b) calcium phosphate. Although efficiencies of transformation achieved to date have been low, these methods may be used as selection of the transformants is possible.

Another method involves fusing bacteria that contain desired plasmids with the plant cells. Such methods involve converting the bacteria into spheroplasts and converting the plant cells into protoplasts. Both of these methods remove the cell wall barrier from the bacterial and plant cells, using enzymatic digestion. The two cell types can then be fused together by exposure to chemical agents, such as polyethylene glycol. Although the transformation efficiencies achieved to date by this method are low, similar experiments using fusions of bacterial and animal cells have produced good results.

Other methods that may be used to genetically transform animal cells involve (a) direct microinjection of DNA into animal cells, using very thin glass needles, and (b) electric-current-induced uptake of DNA by animal cells, or electroporation. These techniques may also be used to transform other eukaryotic cells.

S-adenosylmethionine, herein interchangeably referred to as AdoMet, is active in more than forty biological reactions in vivo. It operates in association with folic acid and vitamin B-12 as a methylating agent, and is also essential for the formation of many sulfur-containing compounds in the body, including glutathione and various components of cartilaginous connective tissue. S-adenosylmethionine has been known to be a substance having a therapeutic effect on jecur adipsum, lipema and arteriosclerosis.

This invention describes a DNA sequence of recombinant plant-yeast hybrid methylene tetrahydrofolate reductase (E.C. #1.5.1.20) that consists of the cDNA sequence encoding for the catalytic aminoterminal domain of yeast MTHFR (MET13), joined to the cDNA sequence encoding the regulatory carboxyterminal domain of MTHFR from the plant *Arabidopsis thaliana* (AtMTHFR-1).

The DNA sequences of MET13 and AtMTHFR-1 are SEQ ID NO.: 1 and SEQ ID NO.3, respectively. The protein sequences of MET13 and ATMTHFR-1 are SEQ ID NO.: 2 and SEQ ID NO.: 4, respectively. The hybrid is coded for by a fusion gene made from a DNA fragment composed of base 826 to base 1824 of SEQ ID NO.: 1 that is fused to another DNA fragment composed of base 1107 to base 1838 of SEQ ID NO.: 3. A 42-base DNA sequence that codes for the 14 amino acid sequence where the two fragments that make up the hybrid are joined is given in SEQ ID NO.: 13. The DNA sequence of SEQ ID NO.: 13 codes for seven amino acids from each fragment that makes up the hybrid.

MET13 encodes an S-adenosylmethionine-sensitive, NADPH dependent enzyme. AtMTHFR-1 encodes an S-adenosylmethionine-insensitive, NADH-dependent enzyme. The hybrid encodes an S-adenosylmethionine-insensitive enzyme that can use both NADPH and NADH, and has novel combined catalytic and regulatory properties of both its parents. When the two yeast genomic MTHFR DNA sequences (genes MET12 and MET13) encoding S-adenosylmethionine-sensitive, NADPH-dependent proteins, are replaced with DNA encoding the hybrid MTHFR, yeast cells accumulate a high level of S-adenosylmethionine.

EXAMPLE

The present invention makes use of a chimeric gene that when incorporated into an appropriate host results in the over production of S-adenosylmethionine, without the need to supply the host with a source of untransformed methionine. The hyperaccumulation of S-adenosylmethionine is accompanied by an increased accumulation of methionine and more than twice the total folate content (as compared to a host expressing a wild-type gene). The overaccumulation of methionine and S-adenosylmethionine in yeast strains engineered with ChimeraI demonstrates that allosteric inhibition of MTHFR by S-adenosylmethionine controls or modifies methylneogenesis, and hence, the commitment of Carbon-1 units to methylneogenesis. Chemicals Used

[$^{14}$C]Formaldehyde (53 mCi mmol$^{-1}$) was purchased from NEN Life Science Products, and (6R, 6S)-[methyl-$^{14}$C]CH$_3$-tetrahydrofolic acid ("CH$_3$-THF") (56 mCI mmol$^1$) from Amersham Pharmacia Biotech; specific radioactivities were adjusted to the desired values with unlabeled compound. (6R, 6S)-THF and (6R, 6S)-CH$_3$-THF were obtained from Schircks Laboratories (Jona, Switzerland). The purity of THF was 86%, estimated by letting the NADH—CH$_2$-THF oxidoreductase reaction go to completion. CH$_3$-THF and $^{14}$CH$_3$-THF were dissolved in 8 mM sodium ascorbate and stored at −80 degrees Centigrade. THF was dissolved just before use in N$_2$-gassed 0.25 M triethanolamine-HCl, pH 7, containing 40 mM 2-mercaptoethanol. Glucose-6-phophate dehydrogenase (recombinant *Leuconostoc mesenteroides* enzyme) and all other biochemicals were from Sigma. Enzyme Isolation All operations were at about 0–10 degrees Centigrade. Yeast cultures were grown to an $A_{600}$ of at least about 1–2, washed, and broken by agitation with glass beads in 100 mM potassium phosphate buffer, pH 6.8 or 7.2, containing 1 mM EDTA, 12–25 micromolar FAD, and 10% (v/v) glycerol (Buffer A) plus 1 mM PMSF. Extracts were cleared by centrifugation (25,000×g, 30 minutes), desalted on PD-10 columns (Amersham Pharmacia Biotech) equilibrated in buffer A, and concentrated if necessary in Centricon-30 units (Amicon). Extracts were stored at −80 degrees Centigrade after freezing in liquid $N_2$; this did not affect MTHFR activity. Protein was estimated by Bradford's method using bovine serum albumin as the standard.

Assays for MTHFR Activity

Assays were made under conditions in which substrates were saturating and product formation was proportional to enzyme concentration and time. NAD(P)H-$CH_2$-THF oxidoreductase activity was measured in reaction mixtures (final volume 20 microliters, in 2-mL screw-cap microcentrifuge tubes) containing 100 mM potassium phosphate buffer, pH 7.2, 0.3 mM EDTA, 4 mM 2-mercaptoethanol, 42 nmol (0.1 μCi) of [$^{14}C$]formaldehyde, 20 nmol of THF, 0.5 nmol of FAD, 4 nmol of NAD(P)H, 20 nmol of glucose 6-phosphate, 0.06 units of glucose-6-phosphate dehydrogenase (1 unit=1 micromole of NADC reduced $min^{-1}$ at pH 7.2, 24 degrees Centigrade), and enzyme preparation.

Blank assays contained no NAD(P)H. The buffer, EDTA, [$^{14}C$]formaldehyde, THF, and 2-mercaptoethanol were mixed and held for 5 minutes at 24 degrees Centigrade in hypoxic conditions (to allow $^{14}CH_2$-THF to form) before adding other components. Reactions were incubated at 30 degrees Centigrade for 20 minutes, and stopped by adding 1 mL of 100 mM formaldehyde.

After standing for 20 minutes at 24 degrees Centigrade (to allow $^{14}C$ to exchange out of $CH_2$-THF), 0.2 mL of a slurry of AG-50($H^+$) resin (1:1 with water) was added to bind $^{14}CH_3$-THF. The resin was washed with 3×1.5 mL of 100 mM formaldehyde, mixed with 1 mL of scintillation fluid, and counted. The counting efficiency was 40%, determined using assays spiked with $^{14}CH_3$-THF.

Construction of Chimeric Enzyme

Figure 1:
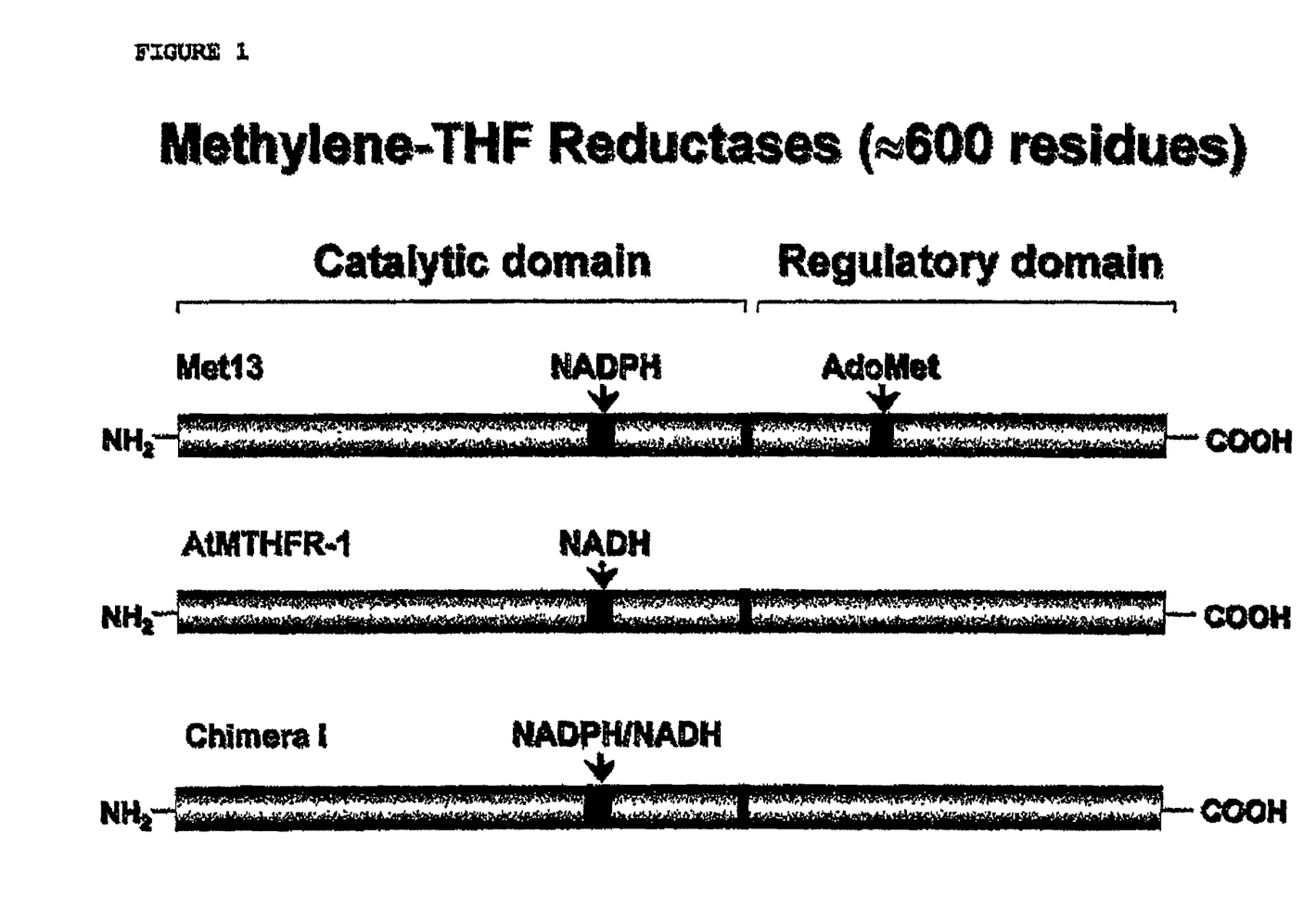
FIG. 1 depicts a map of a chimeric gene in accordance with the present invention.

ChimeraI was constructed by a PCR-based approach. Alternative construction methods such as selective restriction fragment cloning using sticky ends, or even blunt end ligations may also be used. A map of ChimeraI is depicted in FIG. 1. The DNA fragments encoding the N-terminal domain of Met13 (5'-met13 fragment) and the C-terminal domain of AtMTHFR-1 (3'-AtMTHFR-1 fragment) were amplified separately by PCR and joined using a short overlap sequence. The following primer pairs were used:

A. For the amplification of the DNA fragment encoding the N-terminal domain of Met13 (5'-met13 fragment):
>MET13-5PRIME (SEQ ID NO.: 5)
5'-CATGAAGATCACAGAAAAATTAGAGC-3'
>MET13-1-SOER (SEQ ID NO.: 6)
5'-GGTTTGCCCAGAAGATAGGTCTGACTTCC-3'

B. For the amplification of the DNA fragment encoding the C-terminal domain of AtMTHFR-1 (3'-AtMTHFR-1 fragment):
>W43486-1-SOEF (SEQ ID NO.: 7)
5-CCTATCTTCTGGGCAAACCGTCCAAAGAGC-3'

W43486-3PRIME (SEQ ID NO.: 8)
5'TGCACTGCAGTCAAGCAAAGACAGAGAAG-3'
Pst I

The reaction mixtures for PCR amplification contained:
5 μL each primer (5 μM stock)
1 μL dNTP mixture (10 mM stock of each dATP, dGTP, dTTP, and dCTP)
2 μL (5 units) Pfu turbo polymerase (Stratagene)
5 μL 10× buffer for Pfu polymerase
2 μL (100 ng) met 13 cDNA or AtMTHFR-1 cDNA
30 μL water The PCR products were run on 1% low-melting agarose gel, the amplified DNA bands were cut out and purified over the Wizard DNA purification minicolumn (Promega). Final volume of each sample was 50 μL.

The two fragments (5'-met13 and 3'-AtMTHFR-1) were then joined by a second round of PCR as follows:
PCR reaction mix contained:
5 μL MET13-5PRIME primer (5 μM stock)
5 μL W43486-3PRIME primer (5 μM stock)
1 μL dNTP mixture (10 mM stock of each dATP, dGTP, dTTP, and dCTP)
2 μL (5 units) Pfu turbo polymerase (Stratagene)
5 μL 10× buffer for Pfu polymerase
2 μL (out of 50 1L) of the 5'-met13 fragment amplified in the first step of PCR
2 μL (out of 50 μL) of the 3'-AtMTHFR-1 fragment amplified in the first step of PCR
28 μL water The obtained full-length PCR fragment, ChimeraI, was run on 1% low-melting agarose gel, the amplified DNA band was cut out and purified over the Wizard DNA purification minicolumn (Promega).

For the enzyme kinetics studies, the PCR product obtained was inserted into the yeast expression vector pVT103-U as follows: The ChimeraI PCR fragment was digested with PstI restriction enzyme. The digested fragment was run on 1% low-melting agarose gel, cut out, and purified over the Wizard DNA purification minicolumn (Promega).

The yeast expression vector pVT103U was prepared for ligation of the insert as follows: The vector was linearized with BamHI, ethanol precipitated, resuspended in water, and treated with T4 polymerase. Reaction was stopped by heating at 70 degrees Centigrade for 15 minutes, followed by chloroform extraction and ethanol precipitation. The fragment was then resuspended in water and digested with Pst I, run on 1% low-melting agarose gel and purified over the Wizard column as before.

The purified vector (pVT103U) fragment and the purified ChimeraI fragment were mixed, ligated overnight, and introduced by electroporation into competent *E. coli* DH10B cells. The identity of the construct was verified by restriction digests and by DNA sequencing.

The resulting construct (pChimeraI) was then introduced into RRY3 (Δmet12Δmet13) yeast strain for expression and enzyme kinetics studies.

Strain Construction

The pVT-Chimeral plasmid containing the yeast MET13 gene with its putative regulatory carboxyl terminal domain replaced by the corresponding domain of the AtMTHFR-1 gene from *Arabidopsis thaliana* was used as template for construction of strains RRY4 and RRY5. The Chimeral gene (CHIMERAL) was amplified with primers 5'-CAACAGGT-TCATGCCACTGG-3' (MTR2.1, SEQ ID NO.: 9) and 5'-ACAATGGAAAAGGAAGGAGCAAAATCTGGT- AAAAATTCTCGGAGATCAAGCA-3', (Chimera-R1, SEQ ID NO.: 10); sequence homologus to yeast MET13 gene in bold).

The 1.4 Kbp CHIMERAI fragment was gel purified using the QIAquick gel extraction kit (Qiagen) and used to transform the methionine requiring strains RRY1 (MET12 Δmet13) and RRY3 (Δmet12 Δmet13). Transformants were selected by methionine prototrophy indicating successful integration of the CHIMERAI fragment at the disrupted met13 locus. Integration was confirmed by PCR on genomic DNA from RRY4 (MET12 CHIMERAI) and RRY5 (Δmet12 CHIMERAI) using primers 5'-AAGGT-GATATTTCGCTCGTGG-3'(M13-USF, SEQ ID NO.: 11) and 5'-ATGGATCCGGGTGTTAACCAA-3'(M13-DSR, SEQ ID NO.: 12).

Preparation of Extracts for NMR Analysis

Yeast were grown in 500 mL cultures supplemented with $^{13}$C-labeled glycine or formate as indicated. Cells were harvested at an $OD_{600}$ of approximately 3-5 and washed with sterile water. Extracts used for measurement of labeled choline and purines were prepared by resuspending the cell pellets in 30 mL of 0.3 N HCl and heating over a steam bath for 1.5 hours. Samples were centrifuged for 10 minutes at 10,000× g to pellet the cellular debris. The supernatant was evaporated in a Rotavapor-R evaporator, dissolved in 1 mL $D_2O$, and submitted for NMR analysis.

Extracts used for measurement of $^{13}$C-labeled S-adenosylmethionine were prepared by resuspending the cell pellet in 500 mL sterile water and lysing the cells with glass beads by vortexing continuously at 4 degrees Centigrade for 20-30 minutes. Lysates were clarifed by centrifugation at 13,000× g for 15 minutes. Proteins were precipitated by adding 95% ethanol to a final concentration of approximately 60-70% to the crude extract. The samples were incubated on ice for 20 minutes and precipitated proteins were collected by centrifugation at 13,000× g for 15 minutes. The supernatant was evaporated down, dissolved in $D_2O$ and used to measure the $^{13}$C labeling of S-adenosylmethionine via NMR.

NMR Analysis

NMR spectra were obtained on a Varian Unity-Inova Spectrometer with an $^1$H frequency of 500 MHz and a $^{13}$C frequency of 125 MHz. $^{13}$C data were collected with an acquisition time of 1.3-sec with a 3-sec delay and 90 degree pulse angle. Two level composite pulse was used for proton decoupling with a power level of 48 dB during acquisition and 40 dB during delay. A total of 200-2000 scans of 64K data points were acquired over a sweep width of 25 kHz. Data processing included exponential line broadening of 1 Hz.

Figure 2:
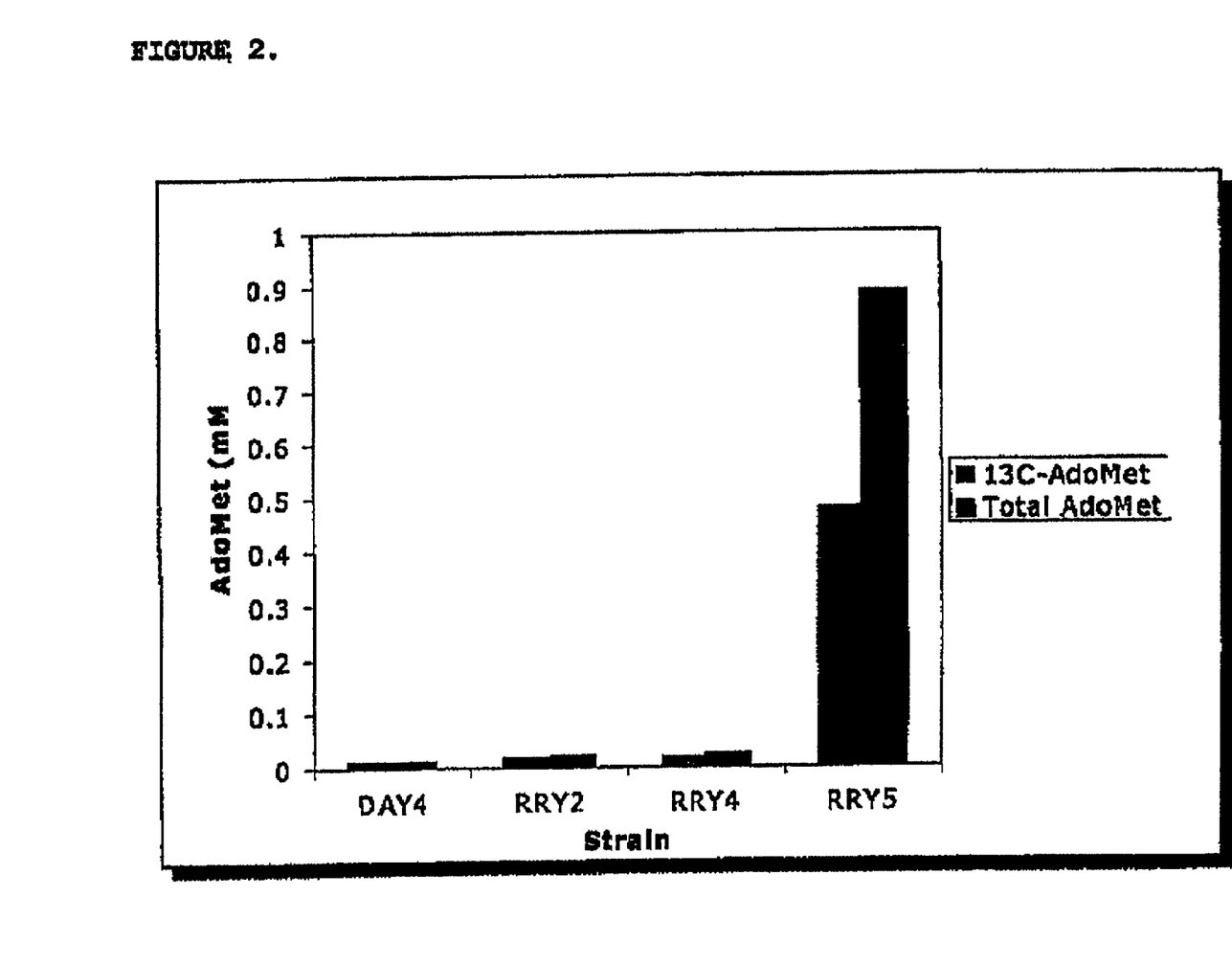
FIG. 2 depicts the concentration of $^{13}$C-labeled and total S-adenosylmethionine in protein free extracts of host strains DAY4, RRY2, RRY4 and RRY5.

Metabolites were identified based on the value of the chemical shifts observed from the natural abundance spectra of standard samples. The extent of the labeling of choline and purines was determined by dividing the peak integral values of the various labeled positions (C1 and C4 for choline; C2 and C8 for purines) by the peak integral value at the position derived directly from glycine (C2 for choline and C5 for purines). The ratios were normalized by dividing the sample ratio by the same ratio derived from the natural abundance spectra of a standard sample. The amount of $^{13}$C-labeled S-adenosylmethionine was calculated by comparing the NMR peak heights to a standard sample of known concentration. FIG. 2 depicts a comparison of the concentration of $^{13}$C labeled and total S-adenosylmethionine in protein free extracts of hosts strains DAY4, RRY2, RRY4 and RRY5.

HPLC Analysis

The method of Wise, et al. was used to measure the concentration of S-adenosylmethionine in protein-free extracts using HPLC. Twenty μl of sample was injected into a Waters HPLC attached to a Waters Spherisorb ODS2, 250×4.6 mm (5 μm particle size) column with a guard column. A Waters Lambda-Max Model 481 LC Spectrophotometer was used for detection at 254 nm. The mobile phase consisted of 50 mM $NaH_2PO_4$, 10 mM heptanesulfonic acid (Sigma) and 20% methanol adjusted to a pH of 4.38 with phosphoric acid. Samples were run at a rate of 0.8 mL/min. Standard samples of S-adenosylmethionine (Sigma) ranging from 2.3 to 210 μg/mL in deionized $H_2O$ were run before the experimental samples.

Determination of Methionine

To determine methionine, 200-mg samples of wet cells were suspended in 180 μL of water and heated at 100 degrees Centigrade for 5 minutes. After cooling on ice, cells were extracted essentially as above except that protein was precipitated with 5-sulfosalicylic acid (final concentration 3.5%). The deproteinized samples were submitted to Biosynthesis Inc. (Lewisville, Tex.) for amino acid analysis using a Beckman 7300 analyzer.

Figure 3:
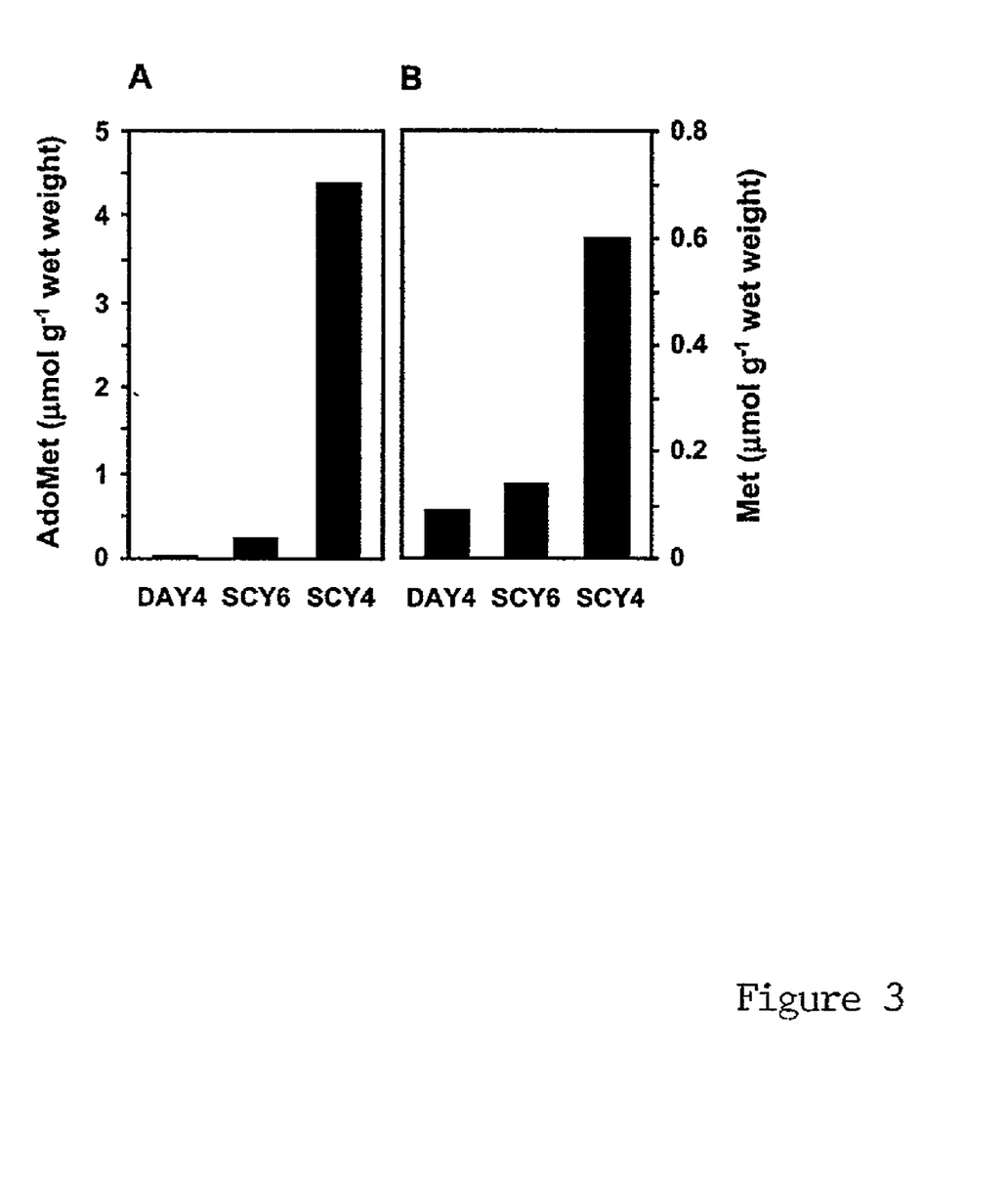
FIG. 3 depicts intracellular levels of S-adenosylmethionine (A) and free methionine (B) in yeast strains DAY4, SCY6 and SCY4.

Intracellular levels of S-adenosylmethionine (A) and free methionine (B) in yeast strains DAY4, SCY6 and SCY4 are shown in FIG. 3. Cells were grown in synthetic minimal medium supplemented with glycine, formate, leucine, histidine, trytophan, and uracil and harvested at an absorbance reading of 2.6–2.9 (at 600 nm) (Roje S, et al., Metabolic Engineering in Yeast Demonstrates That S-Adenosylmethionine Controls Flux Through the Methylenetetrahydrofolate Reductase Reaction in Vivo, 2002 277:4056-61, relevant portions incorporated herein by reference). S-adenosylmethionine data are means of duplicate determinations on the same samples with standard error values less than or equal to 1% of the means. Strain SCY4 expressing the chimeric MTHFR hyperaccumulated S-adenosylmethionine compared to strain DAY4. The hyperaccumulation was observed in cultures harvested at a range of cell densitites; its magnitude varied from 75-fold to 254-fold above wild-type in four independent experiments. In addition, this strain accumulated 7-fold more methionine than DAY4.

Folate Determination

Yeast strains were grown, harvested, and washed as described above for S-adenosylmethionine and methionine determination. Pelleted cells were suspended in twice their wet weight of extraction buffer (50 mM HEPES, 50 mM 2-(cyclohexylamino)ethanesulfonic acid, 0.2 M 2-mercaptoethanol, and 2% (w/v) sodium ascorbate, pH 7.9). Glass beads were added at 1.5 times the wet weight of the pellet. The samples were heated at 100 degrees Centigrade for 10 minutes and lysed by votexing for 4 minutes. After centrifugation at 20,000× g for 30 minutes, supernatants were decanted, their volumes were measured, and they were stored at −70 degrees Centigrade until analysis. Folate species were separated by HPLC and quantitated using the *Lactobacillus casei* microbiologic assay.

Yeast were grown in minimal medium supplemented with glycine, formate, leucine, histidine, tryptophan, and uracil. Folate species as determined by HPLC are shown in the TABLE where data are means of duplicates.

TABLE

Folate Levels in DAY4 and SCY4 Yeast Strains

| Strain | 10-CHO-THF | THF | 5-CHO-THF | 5-CH$_3$-THF |
|---|---|---|---|---|
| DAY4 (MET13) | 6.5 | 4.3 | 6.2 | 49.2 |
| SCY4 (Δmet13 CHIMERA-1) | 19.9 | 14.1 | 13.5 | 108.4 |

All units in nmol/g (wet weight)

The TABLE illustrates that the most abundant folate in all strains was 5-CH$_3$-THF, constituting at least or more than 68% of the total folate pool. The most striking difference between strains was that SCY4 expressing Chimera1 had more than twice the total folate content of the wild-type strain DAY4, although the relative amounts of the individual folates were essentially unchanged.

Although the invention has been described in connection with specific embodiments, it should be understood that the invention as claimed should not be unduly limited to such specific embodiments. Modifications and variations of the described compositions and methods of the invention will be apparent to those skilled in the art without departing from the scope and spirit of the invention. Indeed, various modifications of the described compositions and modes of carrying out the invention that are obvious to those skilled in molecular biology or related arts are intended to be within the scope of the following claims.

What is claimed:

1. A fused gene encoding for methylene tetrahydrofolate reductase consisting of an N-terminal catalytic domain of methylene tetrahydrofolate reductase linked to a C-terminal regulatory domain of methylene tetrahydrofolate reductase, wherein the catalytic domain is encoded by nucleotides 826–1824 of SEQ ID NO: 1 and the regulatory domain is encoded by nucleotides 1107–1830 of SEQ ID NO: 3.

2. The fused gene recited in claim 1, wherein the encoded chimeric protein is able to use cofactors selected from the group consisting of NADPH and NADH.

3. A fused gene comprising the fused gene of claim 1 and 3' and 5' flanking regions.

4. A recombinant DNA vector comprising the fused gene recited in claim 1.

5. A recombinant host cell comprising the recombinant DNA vector recited in claim 4.

6. The recombinant host cell recited in claim 5, wherein the host cell is selected from the group consisting of yeast strains DAY4, RRY2, RRY4 and RRY5.

7. The recombinant host cell recited in claim 5, wherein the cell is selected from the group consisting of prokaryote and eukaryote.

8. The recombinant host cell recited in claim 5, wherein the cell is selected from the group consisting of plant, mammal, and yeast.

9. A plasmid containing the fused gene recited in claim 1.

10. The fused gene recited in claim 1, wherein the fused gene is insensitive encoded methylene tetrahydrofolate reductase is not inhibited by S-adenosylmethionine.

* * * * *